(12) United States Patent
Altwirth

(10) Patent No.: US 6,503,312 B2
(45) Date of Patent: Jan. 7, 2003

(54) ADHESIVE FOR DENTURES AND METHOD FOR ITS PRODUCTION

(76) Inventor: Oskar Altwirth, Oberach 37, 4-4950 Altheim (AT)

(*) Notice: Subject to any disclaimer, the term of this patent is extended or adjusted under 35 U.S.C. 154(b) by 0 days.

(21) Appl. No.: 09/833,129

(22) Filed: Apr. 11, 2001

(65) Prior Publication Data

US 2001/0029871 A1 Oct. 18, 2001

(30) Foreign Application Priority Data

Apr. 12, 2000 (AT) .............................................. 630/00

(51) Int. Cl.[7] ........................... C09K 3/00; A61C 13/23; A61C 13/263
(52) U.S. Cl. ...................... 106/35; 433/180; 106/270; 106/271; 106/272
(58) Field of Search ........................... 106/35, 270, 271, 106/272; 433/180

(56) References Cited

U.S. PATENT DOCUMENTS 4,664,630 A * 5/1987 Lokken ........................ 106/35

* cited by examiner

Primary Examiner—Elizabeth D. Wood
(74) Attorney, Agent, or Firm—Collard & Roe, P.C.

(57) ABSTRACT

An adhesive for dentures comprising a paste-like carrier substance to which hydrocolloids are admixed. In order to obtain an adhesive which is entirely benign from a health viewpoint, the carrier substance consists of honey mixed with alcohol.

9 Claims, No Drawings

ADHESIVE FOR DENTURES AND METHOD FOR ITS PRODUCTION

1. FIELD OF THE INVENTION

The invention relates to an adhesive for dentures with a paste-like carrier substance, to which are added hydrocolloids, and to a method for producing such an adhesive.

2. DESCRIPTION OF THE PRIOR ART

Known denture adhesives comprise petrolatum, paraffin oils, white oil and the like as carrier substances, to which carrier substance are added copolymers made of vinyl chloride, vinyl methylether, polyvinyl acetate and the like in order to increase the adhesive effect. As a result of the penetration of saliva these adhesives are rinsed off the denture over time and reach the stomach, so that after daily use over several years a health hazard arises. The addition of hydrocolloids which are to bind the saliva can delay such rinsing, but not prevent it.

3. SUMMARY OF THE INVENTION

The invention is therefore based on the object of providing an adhesive of the kind mentioned above which even in the case of permanent use does not entail any health hazard. Moreover, a method for the rational production of said adhesive is to be provided.

This object is achieved by the invention in that the carrier substance comprises honey mixed with alcohol, and preferably containing beeswax. Edible hydrocolloids, such as sodium carboxymethyl cellulose, sodium alginate, guar seed flour or the like, are added to the carrier substance.

In accordance with the invention, an edible adhesive is obtained which, even in the case of being washed away from the denture and swallowed, cannot lead to any health hazard. In order to achieve the required stability of the carrier substance and thus being able to utilize its adhesive force to the full extent, the honey mused must substantially lose its water solubility, which entails a change to the structure of the honey. This change is effected by the addition of alcohol, which leads to an esterification or waxification of the honey. By adding beeswax, it is then possible to further reduce the limited water solubility and, by the addition of edible hydrocolloids, penetrating humidity is absorbed and bound in the usual manner. Thus the durability of the adhesive effect is prolonged. Preferred hydrocolloids are sodium carboxymethyl cellulose, which is used in the production of icecream, or sodium alginate E 401, which can also be used in the production of soups, or guar seed flour, which is also used for producing delicatessen foodstuffs. The resultant denture adhesive has a perfect and sufficiently long adhesive effect, is completely tasteless and, therefore, dose not need any addition of flavors.

In order to produce the adhesive, the honey is heated in accordance with the invention until a dry solid honey mass is obtained and alcohol is added to the honey mass. After the complete absorption of the alcohol by the honey mass, the alcohol-honey mass is again dried by heating and comminuted into powder and thereafter the alcohol-honey powder is mixed into a paste-like mass by stirring under addition of alcohol, whereupon said mass forming the carrier substance is heated and mixed with hydrocolloids. In order to limit the water solubility of the honey to the required extent, the honey is heated first until a dry solid mass is obtained, whereupon pure alcohol is added to said dry solid honey mass. In order to ensure that the alcohol can be absorbed completely, it is necessary that the honey mass which is treated with alcohol is allowed to stand for not less than 24 hours in a hermetically sealed manner. A process of esterification or waxification of the honey occurs, which reduces the water solubility and makes the mass tasteless. After the absorption of the alcohol the alcohol-honey mass is heated again, so that residual alcohol will evaporate and a solid mass is obtained again which is then comminuted and ground into a powder in a suitable mill. The alcohol-honey powder is then placed in a stirrer where under the addition of alcohol it is mixed until a paste-like mass is obtained which is spreadable and can be used as a carrier substance. It is then only necessary to mix the hydrocolloids into said paste-like mass and the adhesive is finished.

It is particularly advantageous if in addition to the production of alcohol-honey powder a powder mixture made of dry honey powder and beeswax powder is prepared and said powder mixture is added to the alcohol-honey powder before the alcohol-honey powder is mixed under the addition of alcohol. The beeswax offered on the market in small plates is ground into powder and thoroughly mixed with the dry honey powder. Dry honey powder is understood as vacuum-dried and pulverized honey which is mixed with 20% by weight of lactose. The power mixture thus obtained is then added to the alcohol-honey powder and mixed with said alcohol-honey powder by the addition of alcohol into the carrier substance. The dry honey powder has a low water solubility, and thus also reduces the water solubility of the adhesive honey and facilitates the introduction of the beeswax into the honey mass.

Favorable production conditions are obtained when honey is heated to 200° C. for producing the alcohol-honey powder and the dried honey mass is mixed with alcohol at equal parts by weight, when for preparing the powder mixture 100 parts by weight of dry honey powder and 14 parts by weight of beeswax powder are mixed together and thereafter 20 parts by weight of powder mixture are added to 100 parts by weight of alcohol-honey powder, when 30 parts by weight of alcohol are added to 100 parts by weight of the powder mass of alcohol-honey powder and the powder mixture and the mixture thus obtained is mixed slowly, preferably up to 12 hours, and up to 60 parts by weight of hydrocolloids are added to 100 parts by weight of the paste-like mass, with the mass being heated to approx. 30 to 40° C.

To produce the adhesive, the honey is, therefore, heated in a suitable vessel up to 200° C. until a dry solid mass is obtained whereupon 100 parts by weight of pure alcohol are added to 100 parts by weight of said honey mass. The alcohol is slowly absorbed by the honey mass, the alcohol-honey mass remaining well-enclosed for at least 24 hours until the alcohol has been fully absorbed. The alcohol-honey mass is thereafter heated to approx. 120° C. in order to allow the residual alcohol to evaporate, and dried until a solid mass is obtained again. It is now comminuted and ground into alcohol-honey powder is prepared, with 14 parts by weight of beeswax powder being added to 100 parts by weight of dried honey powder, which powder mixture is now mixed with the alcohol-honey powder; 20 parts by weight of the powder mixture are added to 100 parts by weight of alcohol-honey powder. This overall mixture is thereafter placed in a stable stirrer, where 30 parts by weight of alcohol are added to 100 parts by weight of the mixture and are mixed until a paste-like mass is obtained, which is the carrier substance, which may take up to 12 hours. Thereafter, edible hydrocolloids are added to said paste-like carrier substance by adding at least 60 parts by weight of hydrocolloids to 100 parts by weight of carrier substance, with the carrier substance being heated to approx. 30 to 40° C. for the purpose of thoroughly mixing the hydrocolloide with the carrier substance.

An edible and benign adhesive is thus obtained, which is tasteless, offers a perfect adhesive effect and substantially only consists of honey or honey powder, beeswax, alcohol and edible cellulose or similar hydrocolloids.

What is claimed is:

1. An adhesive for dentures, which comprises a carrier paste comprising honey mixed with alcohol, and an edible hydrocolloid.

2. The adhesive of claim 1, wherein the carrier paste further comprises beeswax.

3. The adhesive of claim 1, wherein the edible hydrocolloid is selected from the group consisting of sodium carboxymethyl cellulose, sodium alginate and guar seed flour.

4. A method of producing an adhesive for dentures, which comprises the steps of (a) heating honey until a dry solid honey mass is obtained, (b) adding alcohol to the dried solid honey mass and permitting the complete absorption of the alcohol in the dried solid honey mass, (c) heating the dried solid honey mass into which the alcohol has been completely absorbed until the mass is dried, (d) comminuting the dried mass into a powder, (e) mixing alcohol with the powder and stirring the mixture until a paste is obtained, and (f) heating the paste while a hydrocolloid is mixed with the heated paste.

5. The method of claim 4, comprising the further steps of preparing a mixture of dry honey powder and beeswax powder, and adding the mixture to the powder comprised of the honey and alcohol before the powder comprised of the honey and alcohol is mixed with alcohol and stirred until a paste is obtained.

6. The method of claim 5, wherein the mixture is prepared by mixing 100 parts by weight of the dry honey powder and 14 parts by weight of the beeswax powder, and 20 parts by weight of the mixture is added to 100 parts by weight of the powder comprised of the honey and alcohol.

7. The method of claim 4, wherein the honey is heated to a temperature of about 200° C. until a dry solid honey mass is obtained, and alcohol is added to the dried solid honey mass in equal parts by weight.

8. The method of claim 4, wherein 30 parts by weight of the alcohol are mixed with 10 parts by weight of the powder and the mixture is stirred for up to 12 hours.

9. The method of claim 4, wherein the paste is heated to about 30° C. to 40° C. while 60 parts by weight of the hydrocolloid is mixed with 100 parts by weight of the heated paste.

* * * * *